United States Patent [19]
Emmerling et al.

[11] Patent Number: 6,126,921
[45] Date of Patent: Oct. 3, 2000

[54] HAIR TREATMENT FORMULATIONS CONTAINING A WATER-INSOLUBLE POLYMER HAVING A GLASS TRANSITION TEMPERATURE OF −20° C. TO 70° C.

[75] Inventors: Winfried Emmerling, Neuss; Hans-Peter Hofmann, Duesseldorf; Rainer Kade, Solingen; Ludwig Schieferstein, Ratingen, all of Germany

[73] Assignee: Henkel Kommanditgesellschaft auf Aktien, Dusseldorf, Germany

[21] Appl. No.: 08/732,380

[22] PCT Filed: Apr. 18, 1995

[86] PCT No.: PCT/EP95/01437

§ 371 Date: Oct. 25, 1996

§ 102(e) Date: Oct. 25, 1996

[87] PCT Pub. No.: WO95/28908

PCT Pub. Date: Nov. 2, 1995

[30] Foreign Application Priority Data

Apr. 26, 1994 [DE] Germany ............... 44 14 424

[51] Int. Cl.[7] ............... A61K 9/12; A61K 7/075
[52] U.S. Cl. .............. 424/47; 424/70.11; 424/70.16
[58] Field of Search ................ 424/47, DIG. 1, 424/DIG. 2, 78.02, 70.11, 70.16; 514/957

[56] References Cited

U.S. PATENT DOCUMENTS

| | | | |
|---|---|---|---|
| 4,324,780 | 4/1982 | Jacquet et al. | 424/47 |
| 4,814,101 | 3/1989 | Schieferstein et al. | 252/174.23 |
| 4,897,262 | 1/1990 | Nandagiri et al. | 424/70.11 |
| 5,021,238 | 6/1991 | Martino et al. | 424/DIG. 2 |
| 5,059,414 | 10/1991 | Dallai et al. | 424/70.11 |
| 5,094,838 | 3/1992 | Benson et al. | 424/DIG. 1 |
| 5,126,126 | 6/1992 | Varaprath et al. | 424/47 |
| 5,176,898 | 1/1993 | Goldberg et al. | 424/47 |
| 5,498,690 | 3/1996 | Kim et al. | 528/296 |
| 5,614,173 | 3/1997 | Ulmer et al. | 424/47 |

FOREIGN PATENT DOCUMENTS

| | | |
|---|---|---|
| 590 604 | 4/1994 | European Pat. Off. . |
| 2 122 074 | 8/1972 | France . |
| 2 150 557 | 6/1972 | Germany . |
| 28 17 369 | 10/1978 | Germany . |
| 37 08 451 | 10/1988 | Germany . |
| 39 29 973 | 3/1991 | Germany . |
| 42 24 761 | 2/1994 | Germany . |
| 851 773 | 10/1960 | United Kingdom . |
| 91/15186 | 10/1991 | WIPO . |
| 91/15187 | 10/1991 | WIPO . |
| 92/21319 | 12/1992 | WIPO . |
| 93/03703 | 3/1993 | WIPO . |
| 94/01079 | 1/1994 | WIPO . |
| 94/02112 | 2/1994 | WIPO . |

OTHER PUBLICATIONS

Martino, G. T et al. (1992). Spray Technology & Marketing, Mar. Issue, pp. 34–39.

Johnsen, M.A. (1992). Spray Technology & Marketing, Jun. Issue, pp. 32–40.

*Primary Examiner*—Thurman K. Page
*Assistant Examiner*—B. Fubara
*Attorney, Agent, or Firm*—Wayne C. Jaescke; Glenn E. J. Murphy; Real J. Grandmaison

[57] ABSTRACT

A process for treating hair by applying thereto a composition in the form of an aqueous dispersion of a water-insoluble polymer having a glass transition temperature of −20° C. to +70° C. wherein the water-insoluble polymer is formed from monomers selected from the group consisting of esters of acrylic acid, esters of methacrylic acid and styrene, and the composition further contains a water-soluble polymer.

5 Claims, No Drawings

HAIR TREATMENT FORMULATIONS CONTAINING A WATER-INSOLUBLE POLYMER HAVING A GLASS TRANSITION TEMPERATURE OF −20° C. TO 70° C.

FIELD OF THE INVENTION

This invention relates to hair treatment formulations in the form of aqueous dispersions of special polymers.

An attractive-looking hairstyle is today generally regarded as an essential part of a groomed appearance. In the context of current fashion trends, "chick" hairstyles are always those which, with many types of hair, can only be created and maintained for prolonged periods using certain setting agents.

These setting agents, which are generally polymeric compounds, may be incorporated in typical hair cleaning and conditioning formulations. In many cases, however, it is of advantage to use them in the form of special formulations, such as setting lotions or hair sprays.

Now, there have recently been a number of developments in the hair cosmetics field which have created a demand for new setting agents or rather new types of formulation. Many of these developments are not attributable to performance-related disadvantages or inadequacies of known formulations, but for example to environmental factors, to legal requirements or to other "non-technical" causes.

Accordingly, there is a need to develop corresponding formulations which meet consumer expectations in regard to their performance properties, for example spray behavior and drying time in the case of hair sprays.

In particular, there is an increasing demand for a change from formulations based on volatile organic compounds, for example alcohols, to water-based formulations.

It has now been found that hair treatment formulations in the form of aqueous dispersions of certain water-insoluble polymers, which additionally contain a dissolved polymer, are eminently suitable for a number of applications.

DESCRIPTION OF THE INVENTION

Accordingly, the present invention relates to hair treatment formulations containing typical cosmetic ingredients in the form of an aqueous dispersion of an insoluble polymer, characterized in that the polymer has a glass transition temperature of −20 to +70° C. and is essentially formed from monomers selected from the group consisting of esters of acrylic acid, esters of methacrylic acid and styrene and in that the hair treatment formulation additionally contains a water-soluble polymer.

Hair treatment formulations in the form of aqueous solutions or emulsions of polymers containing acrylate monomers are known, for example, from International patent applications WO 94/02112 and WO/01079 and from European patent application O 590 604.

In addition, the use of water-soluble or water-dispersible poly-condensates with glass temperatures above +20° C. in hair treatment formulations is known from DE-OS 42 24 761.

Finally, hair sprays in the form of water-based polyester dispersions are known from publication CB-14B of the Eastmann Chemical Company. These hair sprays have the disadvantage that, at high polymer concentrations, the nozzles of the applicator often become blocked after only a short time, particularly in the case of pump sprays. Accordingly, these polymers can only be used in relatively low concentrations in consumer products so that, when the necessary quantities of polymer are applied to the hair, a large amount of water is applied at the same time.

However, none of the cited documents makes any reference to the particularly advantageous properties of the formulations according to the invention.

The hair treatment formulations according to the invention are present in the form of aqueous dispersions and contain an insoluble polymer.

Aqueous dispersions in the context of the present invention are dispersions of which the outer phase consists predominantly of water. The outer phase may additionally contain other water-miscible solvents, for example ethanol and isopropanol. These other solvents are present in quantities of at most up to 10% by weight, based on the formulation as a whole. In a preferred embodiment, the outer phase contains water as sole solvent. Another preferred embodiment contains no more than 5%, based on the formulation as a whole, of other solvents in the outer phase.

In exceptional cases where an only sparingly water-soluble nonionic polymer is to be additionally incorporated in the formulation, the content of other solvents may be up to 20%. In cases such as these, however, it is absolutely essential to ensure that the dispersion is not destabilized. Such destabilization is prevented inter alia by not adding pure or 96% alcohol in the preparation of the formulation. The alcohol component should only be added in the form of a solution with a concentration of 50% or less.

In the context of the invention, a polymer is insoluble if less than 1% by weight dissolves in water at room temperature.

The water-insoluble polymers used in accordance with the invention have glass transition temperatures of −20° C. to +70° C. Polymers with glass transition temperatures of −10° C. to +50° C. and, more particularly, from +10° C. to +30° C. are preferred.

The water-insoluble polymers used in accordance with the invention consist for the most part, i.e. at least 80% by weight, based on the polymer, of esters of acrylic acid and/or methacrylic acid and/or styrene.

Esters of acrylic and methacrylic acid suitable for the purposes of the invention are any known esters of these acids with linear and branched, saturated and unsaturated aliphatic alcohols, aromatic alcohols and aliphatic-aromatic alcohols. Esters with linear and branched, saturated and unsaturated aliphatic alcohols containing 1 to 22 carbon atoms are preferred. Examples of such alcohols are methanol, ethanol, n- and isopropanol, n- and iso-1-butanol, n-1-pentanol, n-1-hexanol, n-1-heptanol, n-1-octanol, n-2-octanol, n-1-decanol, n-1-dodecanol (lauryl alcohol), myristyl alcohol, cetyl alcohol, stearyl alcohol, behenyl alcohol, oleyl alcohol and linoleyl alcohol. Particularly preferred alcohols contain 1 to 6 and, more particularly, 1 to 4 carbon atoms.

Esters of acrylic and methacrylic acid with the corresponding alkoxylated, more particularly ethoxylated, alcohols may also be used in accordance with the invention, but are less preferred. The degrees of alkoxylation may be from 1 to about 10.

Styrenes in the context of the present invention are also compounds which contain a short-chain alkyl group, more particularly a methyl group, at the α C atom of the vinyl group. The content of styrene groups in the polymer is preferably limited to less than 70% by weight, based on the polymer, because otherwise difficulties could be involved in obtaining polymers with glass temperatures in the range mentioned.

One particular advantage is that polymers consisting only of a few monomers may be used in accordance with the invention. Thus, formulations containing homopolymers or copolymers of only two monomers have surprisingly good properties. Accordingly, it may be preferable to use such homopolymers or copolymers for the purposes of the teaching according to the invention.

In a preferred embodiment, therefore, the water-insoluble polymers contain no other structural elements apart from the acrylates, methacrylates and styrenes, impurities of the monomers and chain-terminating compounds not being regarded as further structural elements.

However, it has been found that polymers containing up to 20% by weight and, more particularly, up to 10% by weight of other structural elements may also be used in accordance with the invention. The other structural elements in question may be:

acrylamides and methacrylamides,
acrylic acid, methacrylic acid and alkali metal, alkaline earth metal, aluminium, ammonium and alkylolammonium salts thereof,
crotonic acid, esters and alkali metal, alkaline earth metal, aluminium, ammonium and alkylolammonium salts thereof,
vinyl and allyl compounds,
aminofunctional monomers.

In general, the advantages according to the invention were only observed with those polymers in which the percentage content of other structural elements was limited to less than 5% by weight, based on the polymer. It was also found that, where ionic structural elements were included, it was of advantage for only cationic or only anionic structural elements to be represented in the polymer. These polymers had distinctly better properties than those in which both anionic and cationic structural elements were represented.

In selecting the monomers and the other structural elements, if any, it is absolutely essential to ensure that the glass temperature is in the range from $-20°$ C. to $+70°$ C. The expert is in a position to make the necessary choice in advance without any difficulty on the basis of the known relationships between the glass temperatures of the particular homopolymers and the corresponding copolymers. In the case of polymers containing other ionic structural elements, it is essential to ensure that solubility does not increase too much in order to avoid the resulting disadvantages.

The average molecular weights of the polymers used in accordance with the invention are generally in the range from 20,000 to 2,000,000, molecular weights in the range from 50,000 to 500,000 having proved to be particularly advantageous. The possibilities for obtaining molecular weights in a required range in the synthesis of polymers are well known to the expert.

The hair treatment formulations according to the invention preferably contain the insoluble polymer in quantities of 0.1 to 30% by weight and, more preferably, in quantities of 1 to 20% by weight, based on the formulation as a whole, in dependence upon the type of hair treatment formulation which is not limited in any way.

Even at relatively high concentrations, i.e. at concentrations above about 10%, the formulations according to the invention are distinguished from formulations containing dissolved polymers by very low viscosities. Since it is thus possible to prepare formulations with the high percentage contents of polymers mentioned, the necessary quantity of polymer can be applied to the hair with a comparatively small quantity of water, so that the drying time of formulations remaining on the hair remains in an acceptable range.

The removability in particular of the hair treatment formulations by washing out is distinctly increased if they additionally contain water-soluble polymers. The term "water-soluble" in the context of the invention is understood to mean that the quantity of polymer present in the hair treatment formulation according to the invention is soluble in water at room temperature. In general, distinctly more than 1% by weight of these polymers, which are mentioned in detail hereinafter, is soluble in water.

In a preferred embodiment, the water-soluble polymers are present in the hair treatment formulations according to the invention in quantities of 0.05 to 5% by weight, based on the formulation as a whole. In many cases, quantities of only about 1% by weight or less, based on the formulation as a whole, are sufficient.

In another preferred embodiment, the water-soluble polymers are used in quantities of 1 to 20% by weight, based on the dispersed insoluble polymer.

This water-soluble polymer may even be used as a stabilizer in the emulsion polymerization of the insoluble polymers, i.e. may actually be added during the preparation of the insoluble polymer. However, it is normally added during the production of the hair treatment formulation.

Particularly preferred water-soluble polymers according to the invention are nonionic, particularly where they are added during the production of the hair treatment formulation. Examples of suitable nonionic polymers are:

Polyvinyl pyrrolidones of the type marketed, for example, under the name of Luviskol® (BASF).
Vinyl pyrrolidone/vinyl acetate copolymers of the type marketed, for example, under the name of Luviskol® (BASF). Luviskol® VA 64 and Luviskol® VA 73 are preferred nonionic polymers.
Cellulose ethers, such as hydroxypropyl cellulose, hydroxyethyl cellulose and methyl hydroxypropyl cellulose, of the type marketed, for example, under the names of Culminal® and Benecel®) (AQUALON).

Suitable amphoteric polymers are, for example, the octyl acrylamide/methyl methacrylate/tert.butylaminoethyl methacrylate/2-hydroxypropyl methacrylate copolymers obtainable under the names of Amphomer® and Amphomer® LV-71 (DELFT NATIONAL), although their use is generally confined to neutral or alkaline formulations.

Suitable zwitterionic polymers are, for example, the polymers disclosed in German patent applications DE 39 29 973, DE 21 50 557, DE 28 17 369 and DE 37 08 451. Acrylamidopropyl trimethyl ammonium chloride/acrylic acid or methacrylic acid copolymers and alkali metal and ammonium salts thereof are particularly preferred zwitterionic polymers. Other suitable zwitterionic polymers are methacryl ethyl betaine/methacrylate copolymers which are commercially available under the name of Amersette® (AMERCHOL).

Anionic polymers suitable for the purposes of the invention are inter alia:

Vinyl acetate/crotonic acid copolymers of the type marketed, for example, under the names of Resyn® (NATIONAL STARCH), Luviset® (BASF) and Gafset® (GAF).
Vinyl pyrrolidone/vinyl acrylate copolymers obtainable, for example, under the name of Luviflex®) (BASF). A preferred polymer is the vinyl pyrrolidone/acrylate terpolymer obtainable under the name of Luviflex®) VBM-35 (BASF).
Acrylic acid/ethyl acrylate/N-tert.butyl acrylamide terpolymers of the type marketed, for example, under the name of Ultrahold® strong (BASF).

To secure the advantages according to the invention, the use of anionic polymers is generally also limited to neutral or, more particularly, alkaline solutions.

Cationic polymers are only suitable as soluble polymers in exceptional cases.

In cases where the water-insoluble polymer contains ionic groups, it has proved to be appropriate for the water-soluble polymer to be nonionic or to have the same ionicity.

In some cases, a combination of dispersed anionic polymers and dissolved anionic polymers has proved to be particularly advantageous. In addition, it is preferred in many cases to add the soluble polymer to the otherwise completed formulation.

The other ingredients of the hair treatment formulations according to the invention are dependent upon the type of hair treatment formulation. In principle, the formulations according to the invention encompass all known types of hair treatment formulations such as, for example, setting lotions, hair sprays, styling gel, hair shampoos, hair rinses, hair conditioners, permanent wave sets and hair colorants.

Preferred hair treatment formulations according to the invention are those which remain on the hair after application. These include in particular setting lotions, hair sprays and styling gels. Formulations such as these may also be made up with a propellent to form a foam aerosol.

Other ingredients of the formulations according to the invention may be, for example, anionic surfactants, such as for example fatty alkyl sulfates and ether sulfates, cationic surfactants, such as for example quaternary ammonium compounds, zwitterionic surfactants, such as betaines, for example, ampholytic surfactants, nonionic surfactants, such as for example alkyl polyglycosides and ethoxylated fatty alcohols, structurants, such as glucose and maleic acid, hair-conditioning compounds, such as phospholipids, for example soya lecithin, egg lecithin and kephalins, and also silicone oils, protein hydrolyzates, more especially elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, dyes, anti-dandruff agents, such as Piroctone Olamine and Zink Omadine, other substances for pH adjustment, active agents, such as panthenol, allantoin, pyrrolidone carboxylic acids and salts thereof, plant extracts and vitamins, light stabilizers, consistency regulators, such as sugar esters, polyol esters or polyolalkyl ethers, fats and waxes, such as spermaceti, beeswax, montan wax, paraffins and fatty alcohols, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol monostearate and distearate, propellents, such as propane/butane mixtures, $N_2O$, dimethyl ether, $CO_2$ and air and antioxidants, substantive dyes, so-called primary and secondary intermediates as oxidation dye precursors, reducing agents, such as for example thioglycolic acid and derivatives thereof, thiolactic acid, cysteamine, thiomalic acid and α-mercaptoethane sulfonic acid, oxidizing agents, such as hydrogen peroxide, potassium bromate and sodium bromate.

The present invention also relates to the use of the formulations according to the invention for treating keratin fibers, especially hair.

The following Examples are intended to illustrate the invention.

EXAMPLES

1. Production Examples 1.1 Polymer Dispersion 1

445 g of deionized water, 134 g of G-Cryl® 5000 (a water-soluble copolymer of an aromatic vinyl compound and acrylic acid with a glass transition temperature of around 100° C. (Henkel)) and then, in portions, 30 g of a 25% aqueous ammonia solution were introduced into a reaction vessel equipped with a stirrer, a heating system, a cooling system, a reflux condenser, a thermometer and a stirrable metering vessel. The contents of the reaction vessel were then stirred at room temperature until a homogeneous opaque solution had formed. After repeated evacuation and purging of the reaction vessel with high-purity nitrogen, 10 g of Dowfax 2A1 (4-dodecyl diphenyl ether disulfonate disodium salt, 45% active substance in water (DOW)) were added and the mixture was heated to 85° C. 3.5 g of ammonium peroxydisulfate dissolved in 18 g of deionized water were then added, followed by the uniform introduction over a period of 75 minutes of a mixture consisting of 185 g of methyl methacrylate, 134 g of butyl acrylate and 15 g of Dehydrophen® 65 (nonylphenol +6.5 ethylene oxide (HENKEL)). The temperature of the mixture was kept just below +88° C. by external cooling. When 80% of the monomer emulsion had been added, another 0.5 g of ammonium peroxydisulfate dissolved in 15 g of deionized water were introduced. After the monomer had been added, the mixture was stirred for another 60 minutes at +85° C. After cooling to below +40° C., 10 g of polypropylene glycol (molecular weight around 1000; (DOW)) were added to the resulting dispersion which was then filtered through a Perlon bag filter with a mesh width of 80 μm.

The coagulate-free milky polymer dispersion had a viscosity of around 3000 mPas. The glass temperature of the dispersed polymer was 20° C.

1.2 Polymer Dispersion 2

445 g of deionized water, 134 g of G-Cryl® 5000 (a water-soluble copolymer of an aromatic vinyl compound and acrylic acid with a glass transition temperature of around 100° C. (Henkel)) and then, in portions, 30 g of a 25% aqueous ammonia solution were introduced into a reaction vessel equipped with a stirrer, a heating system, a cooling system, a reflux condenser, a thermometer and a stirrable metering vessel. The contents of the reaction vessel were then stirred at room temperature until a homogeneous opaque solution had formed. After repeated evacuation and purging of the reaction vessel with high-purity nitrogen, 10 g of Dowfax 2A1 (4-dodecyl diphenyl ether disulfonate disodium salt, 45% active substance in water (DOW)) were added and the mixture was heated to 85° C. 3.5 g of ammonium peroxydisulfate dissolved in 18 g of deionized water were then added, followed by the uniform introduction over a period of 75 minutes of a mixture consisting of 123 g of methyl methacrylate, 89 g of 2-ethylhexyl acrylate, 62 g of styrene, 45 g of butyl acrylate and 15 g of Dehydrophen® 65 (nonylphenol +6.5 ethylene oxide (HENKEL)). The temperature of the mixture was kept just below +88° C. by external cooling. When 80% of the monomer emulsion had been added, another 0.5 g of ammonium peroxydisulfate dissolved in 15 g of deionized water were introduced. After the monomer had been added, the mixture was stirred for another 60 minutes at +85° C. After cooling to below +40° C., 10 g of polypropylene glycol (molecular weight around 1000; (DOW)) were added to the resulting dispersion which was then filtered through a Perlon bag filter with a mesh width of 80 μm.

A coagulate-free milky polymer dispersion with a dry residue of 46.9% (as measured with a Mettler LP 15 drying balance for 1 hour at stage 10) and a Brookfield viscosity of around 1500 mPas (as measured with a Brookfield RTV viscosimeter at 20° C./20 r.p.m., spindle 2). The dispersion had a pH value of 8. The glass temperature of the dispersed polymer was 20° C.

1.3 Polymer Dispersion 3

396 g of deionized water and 1.5 g of Disponil® FES 993 (fatty alcohol polyglycol ether sulfate with an active substance content of around 30% in water (HENKEL)) were heated to 82° C. in a reaction vessel equipped with a stirrer, a heating system, a cooling system, a reflux condenser, a thermometer and a stirrable metering vessel. 0.5 g of potassium peroxydisulfate dissolved in 12 g of deionized water were then added. The emulsion described in the following was then uniformly added over a period of 2 hours. The organic phase of the emulsion consisted of 152 g of butyl acrylate, 194 g of methyl methacrylate and 10 g of methacrylic acid while the aqueous phase consisted of 150 g of deionized water, 18.5 g of Disponil® FES 993 and 1 g of potassium peroxydisulfate. The emulsion was prepared by stirring in a metering vessel and was kept stable by continued stirring. During the addition, the temperature of the mixture was kept just below +85° C. by external cooling. After the addition, the mixture was stirred for another 20 minutes at +85° C. 0.5 g of potassium peroxydisulfate dissolved in 12 g of deionized water were then added, followed by stirring for another 45 minutes at +85° C. After cooling to below +40° C., the dispersion was neutralized to a pH value of 6.5 with around 5 g of 12.5% ammonia solution and was filtered through an 80 μm mesh Perlon bag filter.

A low-viscosity coagulate-free milky polymer dispersion with a dry residue of 38.3% (as measured with a Mettler IR dryer for 1 hour at stage 10) and an average particle size of 115 nm was obtained. The dispersed polymer had a glass temperature of around 20° C.

2. Performance Tests 2.1 Curl Retention Test
2.1.1. Test Procedure

The measurement was carried out on 5 hair tresses (#6925 of Fischbach und Miller; weight 0.5 g, length 28 cm) at 22° C./90% relative air humidity.

The weighed dried tress was immersed in the polymer dispersion (5% by weight of polymer) to be investigated, uniform distribution being ensured by repeated immersion and removal. The excess polymer dispersion was stripped off between the thumb and index finger and the tresses were adjusted to a weight increase of around 0.3 g (based on the untreated tress). The moist tress was then wound onto a spiral curler (diameter around 7 mm) and dried overnight. The curled tress was then removed and hung for 24 hours at 22° C./90% relative air humidity.

The curl retention value is then calculated on the basis of the following relation:

$$c_r = (l - l_{24})/(l - l_0) \cdot 100$$

where
  l is the length of the tress between the 1st and 5th wave centers in the stretched state
  $l_{24}$ is the distance between the 1st and 5th wave centers after hanging for 24 hours and
  $l_0$ is the distance between the 1st and 5th wave centers immediately after removal of the spiral curler.

Curl retention values of 58 and 60% were obtained with the dispersions of Examples 1.2 and 1.3.

A high curl retention level is also obtained when the dispersions are varied in regard to the Tg range mentioned. At very low Tg values, the films are too soft while, at very high Tg values, they are too brittle. In both cases, there is also a distinct deterioration in the curl retention values.

2.2.2. Removability by Washing

After 24 hours, hair tresses (#6923 of Fischbach und Miller; weight about 2 g, length about 15 cm) which had been sprayed with the formulations to be investigated (1 g of spray containing 20% by weight of polymer) were washed with a surfactant solution (10% Texapon®N 28 (sodium lauryl ether sulfate, 28% active substance in water (HENKEL)) in water, dried and visually examined for residues.

The dispersions of Examples 1.1 and 1.2 were readily washed out.

The dispersion of Example 1.3 showed residues. By contrast, a dispersion which could be completely washed out was formed by addition of 1% of Luviskol® VA 64 (vinyl acetate/vinyl pyrrolidone copolymer (BASF)).

2.2.3. Sprayability

All the dispersions were readily sprayable even at high polymer concentrations (20%). The nozzles did not clog up even after prolonged use.

3. Formulations

All Figures are Parts by Weight
3.1 Pump Spray
Panthenol 0.5
Perfume oil 0.2
Luviskol®VA 64[1] 1.0
20% dispersion of the polymer
according to Example 1.1 to 100
[1] Vinyl acetate/vinyl pyrrolidone copolymer (BASF)
3.2 Pump Spray
Panthenol 0.5
Perfume oil 0.2
20% dispersion of the polymer
according to Example 1.2 to 100

What is claimed is:

1. A hair treatment composition consisting essentially of an aqueous dispersion containing 0.1% to 30% by weight of a water-insoluble polymer having a glass transition temperature of $-20°$ C. to $+70°$ C. and an average molecular weight from 20,000 to 2,000,000, wherein at least 80% by weight of said water-insoluble polymer having been formed from monomers selected from the group consisting of esters of acrylic acid, esters of methacrylic acid and styrene, 0.05% to 5% by weight of a water-soluble polymer, and the balance, water, based on the weight of the composition.

2. A composition as in claim 1 wherein at least 90% by weight of said water-insoluble polymer consists of monomers selected from the group consisting of esters of acrylic or methacrylic acid with $C_{1-22}$ alcohols and styrene, with the proviso that the content of styrene units is not more than 70% by weight, based on the weight of said polymer.

3. A composition as in claim 1 wherein said esters of acrylic and methacrylic acid comprise esters with $C_{1-6}$ alcohols.

4. A composition as in claim 1 wherein said water-insoluble polymer contains at least two different monomers selected from esters of acrylic or methacrylic acid and styrene.

5. A composition as in claim 1 wherein said water-soluble polymer is nonionic.

* * * * *